(12) United States Patent
Bremenstul

(10) Patent No.: US 6,302,111 B1
(45) Date of Patent: Oct. 16, 2001

(54) ATTACHABLE EAR PLUGS

(76) Inventor: Brain W. Bremenstul, 1847 Duke of York Quay, Virginia Beach, VA (US) 23454

( * ) Notice: Subject to any disclaimer, the term of this patent is extended or adjusted under 35 U.S.C. 154(b) by 0 days.

(21) Appl. No.: 09/352,682

(22) Filed: Jul. 14, 1999

(51) Int. Cl.[7] ........................................... A61F 11/00

(52) U.S. Cl. ........................................... 128/864; 128/866

(58) Field of Search ..................................... 128/857, 858, 128/864–868; 181/130, 134, 135

(56) References Cited

U.S. PATENT DOCUMENTS

| | | | | |
|---|---|---|---|---|
| 3,915,166 | * | 10/1975 | McCrink | 128/866 |
| 3,943,925 | * | 3/1976 | Leight | 128/866 |
| 4,916,758 | * | 4/1990 | Ross | 128/866 |
| 5,074,375 | * | 12/1991 | Grozil | 128/864 |

* cited by examiner

*Primary Examiner*—Michael A. Brown
(74) *Attorney, Agent, or Firm*—McGuireWoods, LLP

(57) ABSTRACT

An earplug assembly is provided having an appendage which may securely attach the earplug to an arm of an eyeglass frame. The earplugs are inexpensive and easily replaced, to maintain good hygiene and an adequate ear seal to avoid damaging sound levels.

2 Claims, 1 Drawing Sheet

ATTACHABLE EAR PLUGS

BACKGROUND OF THE INVENTION

1. Field of the Invention

The present invention generally relates to eye and ear protection for use in industrial environments.

2. Background Description

There are many industrial environments, such as auto manufacturers and shipyards, where eye and ear protection are both required. However, within this type of environment there are times when protection is not necessary and may be removed for purposes of communication. Storing and relocating each of these safety components has been problematical. Small earplugs are easily lost and quickly become unhygienic.

SUMMARY OF THE INVENTION

It is therefore an object to provide a pair of earplugs which may be attachable to most glasses as chosen by the wearer. The present invention provides the wearer earplugs that are readily available and easily and completely disposable, to maintain good hygiene and the highest level of hearing protection.

With the present invention a pair of ear plugs is provided in which a flexible appendage connects each plug to an eyeglass frame. As worn, the earplugs, readily available, hanging from the eyeglass frame, are readily available for when the wearer enters high noise environments, and easily retained upon exiting.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
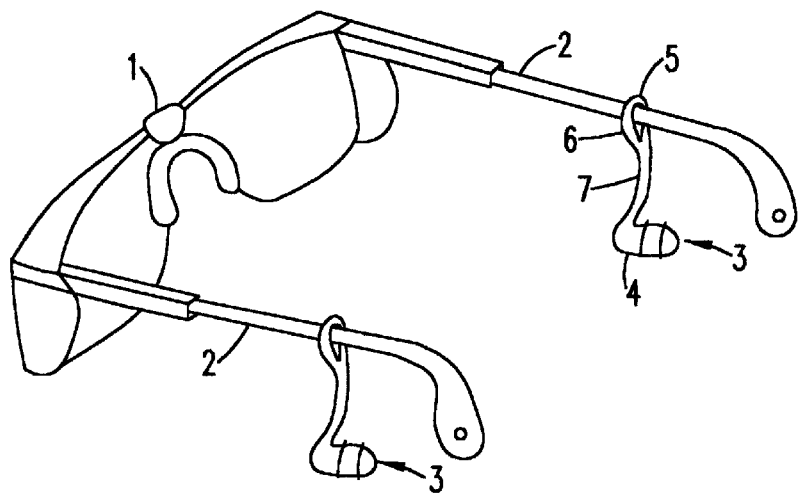
FIG. 1 is an illustration of a pair of eyeglasses with the inventive ear plug to be hung from the frame of the eyeglasses.

Referring now to the drawings, and more particularly to FIG. 1, there is shown a pair of eyeglasses 1 having arms 2. The ear plug 3 has a plug portion 4 and a means for attachment 5 which hooks around an arm 2 of the eyeglasses 1. The means for attachment 5 may be a hole 6 in an appendage 7 of the earplug 3.

Figure 2:
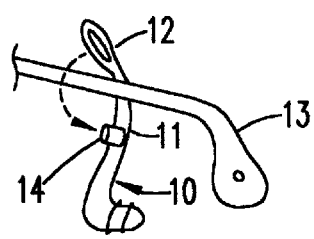
FIG. 2 is an illustration of a second embodiment in which a loop is formed for attaching the plug assembly to an eyeglass frame.

The means for attachment can be implemented in a variety of mechanisms. As shown in FIG. 2, the appendage 11 of the earplug 10 may have a flexible end 12 which can be looped around an arm 13 of a pair of eyeglasses. This flexible end 12 can be snapped, buttoned or otherwise securely attached to itself once wound around the arm of a pair of eyeglasses. In another embodiment the size of the loop around the arm of the pair of glasses may be varied by having a variety of attachment sites 14 for the end of a loop of the appendage. With this embodiment the earplugs can be securely attached to a variety of eyeglass/safety glass arms having varying widths.

Figures 3A, 3B:
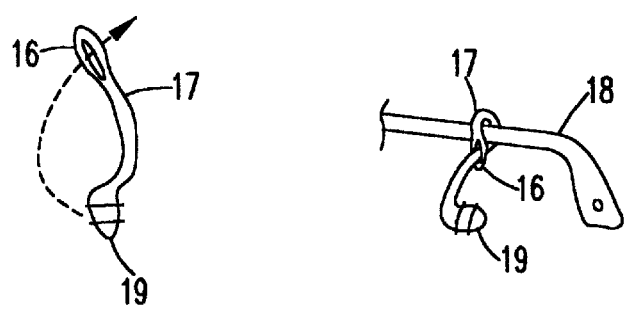
FIGS. 3A and 3B are illustrations of a third embodiment in which the plug assembly is pulled through its own loop as a means of attachment.

In another embodiment shown in FIG. 3A, the means for attachment may be a flexible loop 16 on the end of a flexible appendage 17. As shown in FIG. 3B, after folding the flexible appendage 17 over the eyeglass arm 18, the plug end 19 would be pulled through the flexible loop 16. The plug end 19 is pulled until snugly against the eyeglass arm 18.

While the invention has been described in terms of three embodiments, those skilled in the art will recognize that the invention can be practiced with modification within the spirit and scope of the appended claims.

What is claimed is:

1. An ear plug comprising:

a plug portion;

an appendage extending from said plug portion, said plug portion being positioned at a first end of said appendage;

a first connector positioned on a second end of said appendage; and a second connector positioned on said appendage between said first end with said plug portion and said second end with said first connector, said first and second connectors being joinable together to form a loop for securing said appendage and said plug portion to an eyeglass frame.

2. An ear plug comprising:

a plug portion;

an appendage extending from said plug portion;

a first connector positioned on an end of said appendage, said first connector being selected from the group consisting of buttons, snaps and hooks; and a second connector positioned on said appendage between said plug portion and said end with said first connector, said second connector being selected from the group consisting of buttons, snaps and hooks, said first and second connectors being joinable together to form a loop for securing said appendage and said plug portion to an eyeglass frame.

* * * * *